United States Patent [19]

Hyman

[11] Patent Number: 5,514,569
[45] Date of Patent: May 7, 1996

[54] METHOD FOR ENZYMATIC SYNTHESIS OF OLIGONUCLEOTIDES USING PHOSPHATE PRECIPITATION

[76] Inventor: Edward D. Hyman, Sybtrel Biotechnology, 1500 Edwards Ave. Suite Q, Harahan, La. 70123

[21] Appl. No.: 376,857

[22] Filed: Jan. 23, 1995

Related U.S. Application Data

[63] Continuation-in-part of Ser. No. 259,308, Jun. 13, 1994, which is a continuation-in-part of PCT/US93/12456 Dec. 21, 1993. which is a continuation-in-part of Ser. No. 161,224, Dec. 2, 1993, which is a continuation-in-part of Ser. No. 100,671, Jul. 30, 1993, which is a continuation-in-part of Ser. No. 995,791, Dec. 23, 1992.

[51] Int. Cl.$^6$ ............................ C12P 19/34; C12Q 1/68; C12Q 1/70
[52] U.S. Cl. ................... 435/91.2; 435/5; 435/6; 435/91.1
[58] Field of Search ....................... 435/6, 5, 91.1, 435/91.2; 536/24.3–24.33; 424/94.1, 94.5

[56] References Cited

PUBLICATIONS

Hoopes and McClure, Studies on the Selectivity of DNA Precipitation by Spermine, NAR 9: 5493–5504, 1981.
Storrer, "First Outlines of a Dictionary of Solubilities of Chemical Substances", (1864), Cambridge: Sever and Francis, pp. 488–505.
Dudley, "The Chemical Constitution of Spermine: III. Structure and Synthesis", (1926), Biochemical Journal, 20: 1082–94.
Hyman, "Method and Apparatus for Enzymatic Synthesis of Oligonucleotides", published Jul. 7, 1994, WO94/14972, PCT International Application.
Middleton, "Synthesis and Purification of Oligoribonucleotides Using T4 RNA Ligase and Reverse–Phase Chromatography", (1985), Analytical Biochemistry, 144: 110–7.
Boyer (Fernley), "Mammalian Alkaline Phosphatases", (1971), The Enzymes, Academic Press, 4: 417–47.
Sninsky, "Single addition and transnucleotidation reactions catalyzed by polynucleotide phosphorylase. Effect of enzymatic removal of inorganic phosphate during reaction.", (1974), Nucleic Acids Research, 1: 1665–74.

Razzel, "Studies on Polynucleotides", (1959), Journal of Biological Chemistry, 234: 2105–13.
Kierzek, "Nonenzymatic hydrolysis of oligoribonucleotides", (1992), Nucleic Acids Research, 20: 5079–84.
Stenberg, "Precipitation of Nucleotides by Calcium Phosphate", (1982), Biochemica et Biophysica Acta, 697: 170–3.
Mackey, "New Approach to the Synthesis of Polyribonucleotides of Defined Sequence", (1971), Nature, 233: 551–3.
Futai, "A New Phosphodiesterase Forming Nucleoside 5'-Monophosphate from Rat Liver", (1967), Journal of Biological Chemistry, 242: 5301–7.
Ramaswamy, "(2)3',5'-Bisphosphate Nucleotidase", (1987), Journal of Biological Chemistry, 262: 10044–7.
Brunngraber, "Nucleotides Involved in the Enzymatic Conjugation of Phenols with Sulfate", (1958), Journal of Biological Chemistry, 233: 472–7.

Primary Examiner—W. Gary Jones
Assistant Examiner—Dianne Rees

[57] ABSTRACT

Enzymatic synthesis of a portion of an oligonucleotide is performed by a cycle of synthetic steps: (a) combining an oligonucleotide primer and a blocked nucleotide in a reaction mixture in the presence of a chain extending enzyme, such that a primer-blocked nucleotide product is formed, wherein the blocked nucleotide substrate comprises (i) a nucleotide to be added to form part of the defined sequence and (ii) a blocking group attached to the nucleotide effective to prevent the addition of more than one blocked nucleotide to the primer; and (b) removing the blocking group from the 3' end of the primer-blocked nucleotide product to form a primer-nucleotide product. Phosphate is generated in at least one synthetic step. A precipitate is formed in the cycle comprising phosphate and at least one precipitation cation. The precipitation of phosphate reduces its unfavorable effect on the method. Preferably, cycles of the method are repeated without intermediate purification of primer-nucleotide product or precursor. The precipitation cation may be a polyvalent elemental cation, spermine, or a cation which forms a poorly soluble salt with phosphate. Preferably, the chain extending enzyme is RNA Ligase, the blocked nucleotide is AppNp, and the blocking group is removed using a phosphatase. There is also provided a method for reducing the inhibitory effect of nucleoside 5'-monophosphate and of 3',5'-nucleoside diphosphate on phosphodiesterase I. This is accomplished by enzymatically converting these inhibitors to less inhibitory products.

32 Claims, No Drawings

1

METHOD FOR ENZYMATIC SYNTHESIS OF OLIGONUCLEOTIDES USING PHOSPHATE PRECIPITATION

This application is a continuation-in-part of copending U.S. patent application Ser. No. 08/259,308 filed Jun. 13, 1994, which is a continuation-in-part of copending International Patent Application PCT/US93/12456 filed Dec. 21, 1993 and published Jul. 7, 1994, which is a continuation-in-part of copending U.S. patent application Ser. No. 08/161, 224 filed Dec. 2, 1993, which is a continuation-in-part of copending U.S. patent application Ser. No. 08/100,671 filed Jul. 30, 1993, which is a continuation-in-part of copending U.S. patent application Ser. No. 07/995,791 filed Dec. 23, 1992, all of which are incorporated herein by reference.

BACKGROUND OF THE INVENTION

Synthetic oligonucleotides play a pivotal role in molecular biology, useful especially for DNA sequencing, DNA amplification, and hybridization. A novel method for the synthesis of oligonucleotides has been described previously by the inventor in International Application PCT/US93/12456 and in U.S. patent applications Ser. Nos. 08/259,308, 08/161,224, 08/100,671, 07/995,791. This novel method of the inventor is referred to herein as the "One Pot" method. The One Pot method is expected to replace both the obsolete enzymatic methods and the current chemical methods for making oligonucleotides. The ease with which the One Pot method can be automated will foster a new generation of oligonucleotide synthesizers. These new synthesizers will have increased throughput, increased reliability, and decreased cost per synthesis.

The One Pot method basically involves repeated cycles of (a) extending an oligonucleotide primer using a nucleotide substrate having a 3'-blocking group, thus forming an extended primer with a blocking group at its 3'-end; and (b) removing the 3'-blocking group from the extended primer to prepare the extended primer for the addition of the next nucleotide. When the same nucleotide is to be incorporated in the ensuing cycle, unreacted blocked nucleotide may be reused for the ensuing cycle. In this case, the blocking group is selectively removed from the primer-blocked nucleotide product substantially without deblocking of the unreacted blocked nucleotide. When a different nucleotide is to be incorporated, the method includes the added step of inactivating unreacted blocked nucleotide. Inactivation is performed by converting unreacted blocked nucleotide to a form which is substantially less active as a substrate for the chain extending enzyme than the blocked nucleotide.

In the One Pot enzymatic method, successive cycles of nucleotide addition to an oligonucleotide primer are performed without intermediate purification of oligonucleotide product. By contrast, all previous enzymatic methods teach the need for intermediate purification of oligonucleotide product in each cycle. This advantage of the One Pot method in not requiring intermediate oligonucleotide purification makes the method automatable. However, it has a small disadvantage. After many cycles, phosphate by-product generated by the enzymatic reactions builds to a high level. This phosphate accumulation inhibits several enzymes in the One Pot method, especially alkaline phosphatase (AP).

The inventor's previous approach to the problem of phosphate inhibition was to ensure adequate reaction conditions to completely convert substrate to product. This previous approach reduces the performance of the One Pot method. For example, an extended incubation period or a higher enzyme concentration is required to compensate for the phosphate inhibition. An extended incubation period increases the synthesis time. An increased enzyme concentration increases the cost.

Prior art enzymatic methods for oligonucleotide synthesis have approached the problem of phosphate accumulation by teaching intermediate purification of oligonucleotide product in each cycle. The intermediate purification step removes all phosphate generated in each cycle. For example, Middleton teaches chromatographic purification of oligonucleotide in each cycle, (Middleton et al, 1985, Analytical Biochemistry, 144, p. 114). This prior art approach to the phosphate accumulation problem would erase the automation advantage of the One Pot method. The One Pot method is automatable since it requires only reagent additions to the synthesis solution. Using the prior art approach, the instrument would also need an automated chromatographic purification system. Such an instrument would have a complex construction and a crippled performance.

In the prior art, it is common knowledge that phosphate accumulation causes problems in enzymatic reactions. The phosphate problem is especially detrimental for enzymes which generate phosphate as a by-product. Phosphatases such as alkaline phosphatase are thermodynamically nearly irreversible. The phosphate by-product is well known to strongly inhibit phosphatases (Boyer, 1971, The Enzymes, third edition, Academic Press, v. 4, p. 442). The literature offers no approach to solve this problem, other than cumbersome purification of the product. Other enzymes generate phosphate by-product in a reversible reaction. Such enzymes include polynucleotide phosphorylase and nucleoside phosphorylase. Phosphate by-product accumulation causes reversal of the enzymatic reaction. This reverse reaction reduces the yield of the product of the enzyme forward reaction. For example, nucleoside phosphorylase can be used to synthesize nucleosides from ribose-1-phosphate and a purine base. The phosphate by-product of the reaction can degrade the nucleoside product by the reverse reaction.

Sninsky et al recognized the phosphate problem and devised an approach to remove phosphate (Sninsky et al, Nucleic Acids Research, 1974, 1, 1665–74). Sninsky wanted to improve the coupling yield of oligonucleotide primer and nucleoside diphosphate catalyzed by polynucleotide phosphorylase (PNP). This reaction generates phosphate by-product and is reversible. Sninsky's approach to the phosphate problem was to remove the phosphate enzymatically. A nucleoside and the enzyme nucleoside phosphorylase was added to the reaction mixture. Phosphate by-product of the PNP reaction was converted to ribose-1-phosphate in the presence of the nucleoside and nucleoside phosphorylase. By using this coupled enzyme system, Sninsky improved the yield of the PNP reaction. Sninsky's approach has several disadvantages. First, the nucleoside phosphorylase reaction thermodynamically strongly favors formation of the nucleoside. This severely limits the ability of the second enzymatic reaction to maintain a low phosphate concentration. Second, a long incubation period is needed to remove the phosphate. By the nature of enzymatic reaction, complete equilibrium may require one hour. Third, the removal method is reversible. Phosphate could be re-release from ribose-1-phosphate by a subsequent enzymatic incubation, such as phosphatase. Sninsky avoids the reversibility problem by using an intermediate oligonucleotide purification, which removes ribose-1-phosphate.

Thus, it is well established in the literature that the phosphate by-product of enzymes is deleterious to the performance of the enzymatic reaction. In this context, a useful approach to remove phosphate has been devised by the inventor. This approach solves the prior poor operability of the One Pot method.

OBJECTS OF THE INVENTION

Accordingly, several objects and advantages of the invention are:

(a) to provide a method for removing phosphate by-product generated by the One Pot method by precipitating the phosphate, thereby eliminating the undesirable effect of phosphate, and thereby avoiding the need for intermediate chromatographic purification of oligonucleotide in each cycle;

(b) to provide a method for removing phosphate by-product generated by an enzymatic reaction, thereby eliminating the undesirable effect of phosphate, i.e. inhibition of the enzyme or the reversal of the enzymatic reaction; and (c) to provide a method for removing nucleoside 5'-monophosphate inhibition of the enzyme phosphodiesterase I, by using an enzyme to degrade nucleoside monophosphate.

(d) to provide a method for removing 3',5'-NDP inhibition of the enzyme phosphodiesterase I, by using an enzyme combination to degrade 3',5'-NDP.

Further objects and advantages will become apparent from a consideration of the drawings and ensuing description.

SUMMARY OF THE INVENTION

In accordance with the invention, there is provided a method for enzymatic synthesis of a portion of an oligonucleotide involving a cycle of synthetic steps:

(a) combining an oligonucleotide primer and a blocked nucleotide in a reaction mixture in the presence of a chain extending enzyme, such that a primer-blocked nucleotide product is formed, wherein the blocked nucleotide substrate comprises (i) a nucleotide to be added to form part of the defined sequence and (ii) a blocking group attached to the nucleotide effective to prevent the addition of more than one blocked nucleotide to the primer; and (b) removing the blocking group from the 3' end of the primer-blocked nucleotide product to form a primer-nucleotide product;

whereby phosphate is generated in at least one synthetic step; and whereby a precipitate is formed, said precipitate comprising phosphate and at least one precipitation cation.

Preferably, cycles of the method are repeated without intermediate purification of primer-nucleotide product or precursor. In this case, the primer-nucleotide product of step (b) serves as the oligonucleotide primer in step (a) of the ensuing cycle. The method is preferably performed in a manner which minimizes co-precipitation of the primer-nucleotide product, so that the latter may serve as the primer in the ensuing cycle. The precipitation cation may be a polyvalent elemental cation or spermine or a cation which forms a poorly soluble salt with phosphate. Preferably, the chain extending enzyme is RNA Ligase and the blocked nucleotide is AppNp. In this case, removal of the blocking group is preferably performed by using alkaline phosphatase or 3'-phosphatase.

In accordance with another embodiment of the invention, an enzymatic reaction is performed in a reaction mixture containing a precipitation cation and one or more enzyme substrates, such that phosphate is generated as a reaction by-product, whereby a precipitate is formed comprising the precipitation cation and phosphate. The precipitation of phosphate removes the undesired effect of phosphate on the enzymatic reaction. The precipitation cation may be a polyvalent elemental cation or spermine or a cation which forms a poorly soluble salt with phosphate.

In accordance with the invention, there is provided a method for reducing the inhibitory effect of nucleoside 5'-monophosphates on phosphodiesterase I by using an NMP degrading enzyme. The NMP degrading enzyme may be 5'-Nucleotidase, AMP Nucleosidase, or AMP Deaminase. The preferred NMP degrading enzyme is 5'-Nucleotidase.

In accordance with the invention, there is provided a method for reducing the inhibitory effect of 3',5'-nucleoside diphosphate on phosphodiesterase I by using an enzyme combination. The combination comprises the enzyme 3',5'-bisphosphate nucleotidase plus at least one NMP degrading enzyme. The preferred NMP degrading enzyme is 5'-Nucleotidase.

DETAILED DESCRIPTION OF THE INVENTION

Three separate arts have been well established in the literature. A fourth art has been invented previously by the applicant.

(1) It has been known in the art for over 130 years that some cations, such as polyvalent elemental cations and spermine, form salts with $HPO_4^{-2}$ which are poorly soluble in water (Storer, 1864, First Outlines of a Dictionary of Chemical Solubilities, Sever and Francis, pp. 488–505 and Dudley et al, 1926, Biochemical Journal, 20, p. 1084 and p. 1093).

(2) It is known in the art that numerous enzymes generate phosphate by-product, and that this phosphate by-product inhibits the enzyme or causes the unwanted reverse reaction (Boyer, 1971, The Enzymes, third edition, Academic Press, v. 4, p. 442).

(3) It is known in the art that many polyvalent elemental cations, such as $Ca^{+2}$ and $Mn^{+2}$, are compatible with many enzymes. Such cations may even substitute for the natural enzyme cofactor, which is usually $Mg^{+2}$ (Razzel et al, 1959, Journal of Biological Chemistry, 234, 2109).

(4) The One Pot method for synthesizing oligonucleotides, invented previously by the applicant, generates phosphate by-product.

The invention described herein is a synthesis of these four arts. The result of this synthesis is an improved One Pot method for synthesizing oligonucleotides. In the invention, phosphate, which is generated by the enzymatic steps of the One Pot method, is precipitated from solution. The precipitation of phosphate reduces the solution phosphate concentration. Consequently, the inhibition of the enzymes in the One Pot method by phosphate is reduced.

The One Pot method for the synthesis of oligonucleotides has been described by the inventor in previous applications. Consecutive cycles of the One Pot method are performed without intermediate purification of the oligonucleotide product. This innovation makes the One Pot method suitable for automation, but also causes a problem. Phosphate is generated as a by-product of the One Pot method in each cycle. Three enzymes used in the One Pot method generate phosphate by-product: 5'-nucleotidase, 3'-phosphatase, and alkaline phosphatase. In addition, inorganic pyrophosphatase also generates phosphate by-product if employed. These reactions have been described previously by the inventor. A brief summary of these enzymes is given.

5'-Nucleotidase hydrolyzes AMP, which is generated by the coupling of primer and AppNp in accordance with the reaction: AMP+$H_2O$→adenosine+phosphate. 3'-Phosphatase hydrolyzes the phosphate blocking group from primer-pNp in accordance with the reaction: primer-pNp+$H_2O$→primer-pN+phosphate. Alkaline phosphatase similarly hydrolyzes the phosphate blocking group from primer-pNp. In addition, alkaline phosphatase inactivates AppNp substrate in accordance with the reaction: AppNp+$H_2O$→AppN+phosphate. Alternatively, alkaline phosphatase hydrolyzes AMP and 3',5'-NDP to nucleosides+phosphate. The AMP and 3',5'-NDP are generated by nucleotide pyrophosphatase hydrolysis of AppNp. Thus, phosphate by-product can be generated in any of the three basic steps of the One Pot method: coupling nucleotide substrate to primer (5'-Nucleotidase), coupled primer de-blocking (alkaline phosphatase or 3'-phosphatase), and nucleotide substrate inactivation (alkaline phosphatase).

After many cycles without an intermediate purification step, the phosphate by-product concentration can accumulate to high levels. Alternatively, a synthesis which employs a high AppNp concentration, such as 10 mM, can accumulate a high phosphate concentration during a single cycle. This high phosphate concentration inhibits at least two enzymes in the One Pot method. The inventor has determined that the enzyme phosphodiesterase I is moderately inhibited by phosphate. Another enzyme, alkaline phosphatase, is strongly inhibited by phosphate. The strong inhibition of alkaline phosphatase by phosphate is well documented in the literature (Boyer, 1971, The Enzymes, third edition, Academic Press, v. 4, p. 442). Experiments performed by the inventor demonstrate the severity of the problem. The remaining activity of alkaline phosphatase in the presence of 1 mM, 3 mM, and 10 mM $HPO_4^{-2}$ is 31%, 23%, and 11%, respectively.

This enzyme inhibition by phosphate forces some compromise in the performance of the One Pot method. To compensate for the enzyme inhibition, either the enzyme incubation period must be lengthened or the enzyme concentration must be increased. Increasing the incubation period slows the speed of synthesis. Increasing the enzyme concentration is expensive.

The present invention offers a superior approach to the phosphate problem. Phosphate by-product is precipitated from solution by using a precipitation cation. The precipitation cation may be any cation which forms a poorly soluble salt with phosphate in water. In the presence of a precipitation cation, phosphate by-product of the One Pot method forms a precipitate with the precipitation cation. The precipitation of a phosphate transfers phosphate from the solution phase to the insoluble phase. Although the precipitate is still present in the reaction mixture, the precipitate does not affect the enzymatic reactions. This precipitation reduces the soluble phase phosphate concentration and prevents a phosphate build up. As a consequence, the enzymatic reactions of the One Pot method are not subject to the undesirable effect of phosphate. Thus, even after many cycles of the One Pot method, the performance of the method is not diminished. Phosphate removal by precipitation is amenable to automation. Only reagent additions to the synthesis solution are needed.

This approach overcomes the disadvantages of all previous approaches:

The previous approach of the inventor required more enzyme or longer incubation times to compensate for enzyme inhibition. In the present invention, the concentration of soluble phase phosphate is maintained at a low level. No enzyme inhibition by phosphate results. The performance of the One Pot method is maintained.

The previous approach of Middleton required intermediate oligonucleotide purification to remove phosphate. The present invention requires the addition of the precipitation cation reagent to the synthesis solution. Phosphate precipitation overcomes the disadvantage of intermediate oligonucleotide purification.

The previous approach of Sninsky employed enzymatic removal of phosphate. Its disadvantages included: (a) inefficient phosphate removal, since the equilibrium of the enzymatic removal reaction favors free phosphate, (b) slow phosphate removal, since enzymatic reactions are usually slow, such as 1 hour to reach equilibrium, (c) reversibility of phosphate removal, since the phosphate stored as ribose-1-phosphate can be re-released by phosphatase. The present invention overcomes these disadvantages. The phosphate precipitation method is: (a) efficient, since it lowers the soluble phase phosphate to micromolar concentrations, (b) fast, since the precipitation event occurs in milliseconds, and (c) irreversible, since the precipitates generally cannot redissolve in solution.

In a preferred embodiment of the invention, the precipitation cation is added to the synthesis solution at the beginning of each cycle. The amount of precipitation cation added is sufficient to precipitate all phosphate by-product generated in the cycle. In this manner, the precipitation cation acts as a mop. Any phosphate generated by the reactions of the One Pot method is rapidly precipitated. The phosphate concentration is not allowed to accumulate at any point during the cycle. The enzymes of the method, especially alkaline phosphatase, are never subjected to phosphate inhibition.

Adding the Precipitation Cation

Prior to discussing individual precipitation cations, certain aspects of precipitation cations are the same for all precipitation cations.

In practicing the invention, the precipitation cation can be added to the synthesis reaction in several manners. The precipitation cation can be added before the start of a cycle, in the middle of a cycle, at the end of a cycle. The cation addition may be performed in a continuous slow manner or in one block. The precipitation cation is preferably added to effectively prevent phosphate inhibition of the enzymes. This can be achieved by adding a sufficient amount of cation at the beginning of every cycle so that all the phosphate generated in the cycle will be precipitated. This method has the advantage that phosphate is precipitated as it is generated by the enzyme(s). The phosphate concentration does not accumulate. A small excess of cation over the phosphate generated in the cycle is adequate for this purpose. Alternatively, the precipitation cation may be added at the beginning of one cycle in a sufficient amount to precipitate phosphate for several cycles. This method avoids the need to add cation after each cycle.

Other methods of addition may have certain advantages. For example, if the precipitation cation itself causes enzyme inhibition, the method of addition should minimize the precipitation cation concentration. This can be accomplished by adding precipitation cation in a slow continuous manner to exactly balance phosphate generation. The precipitation cation may also be added in quantities smaller than the phosphate present. This would ensure a low precipitation cation solution concentration, and avoid enzyme inhibition caused by the cation. Alternatively, precipitation cation may be added only in the alkaline phosphatase step, during which the phosphate problem is the most deleterious. The least preferred method is adding precipitation cation at the end of the cycle. The benefits of phosphate removal are realized in the ensuing cycle.

The precipitation cation is added as a concentrated solution of a salt of the cation. The anion of the salt may be chloride, hydroxide, AppNp$^{-4}$ substrate, another anion, or a combination. Most chloride salts are highly water soluble. Using the hydroxide salt has the added advantage of neutralizing acid generated by the One Pot method. Using the AppNp-4 salt adds both nucleotide substrate and precipitation cation from the same feed stock. It also reduces the amount of salt accumulation in the One Pot method. The concentrated salt solution may be completely dissolved or a partially dissolved suspension. If it is a partially dissolved suspension, then it should dissolve readily upon addition to the synthesis solution. For example, it is the observation of the inventor that hydroxide salts tend to be poorly soluble in water. The concentrated hydroxide salt forms a suspension mixture. Upon addition to a buffered synthesis solution at pH 8.0, the salt quickly dissolves.

The equilibrium concentration of phosphate in solution may be adjusted by adjusting the solution concentration of precipitation cation. This equilibrium is governed by the thermodynamic solubility product of the cation phosphate salt. Thus, increasing the solution precipitation cation concentration will lower the soluble phosphate concentration. This may be useful to further reduce phosphate inhibition of the enzyme. For performing the invention, it is recommended that the soluble phosphate concentration be kept below 10 mM. However, it is preferred that the precipitation cation be used in a manner which keeps the solution phosphate concentration at about 0.1 mM. At 0.1 mM phosphate, the inhibition of alkaline phosphatase is low. A concentration of 10 mM precipitation cation is usually adequate in maintaining the phosphate concentration below 0.1 mM.

The oligonucleotide synthesis is usually complete after many cycles of the One Pot method. A small amount of the precipitation cation may remain in the soluble phase of the reaction mixture. In purifying the final oligonucleotide product, it may be useful to remove the residual soluble precipitation cation. In this case, adding excess phosphate to the mixture should be effective in precipitating the remaining soluble phase precipitation cation. The precipitate can be separated from the oligonucleotide by centrifugation or filtration. Note that phosphate is added at the end of the synthesis, after all enzymatic reactions have been completed.

Two different types of cations are demonstrated as useful precipitation cations in the present invention: polyvalent elemental cations and spermine.

Polyvalent Elemental Cations as the Precipitation Cation

Many cations are documented in the literature as forming insoluble salts with phosphate. One known class of such cations is polyvalent elemental cations. The insolubility in water of phosphate salts (HPO$_4^{-2}$) of several polyvalent elemental cations has been known for over 130 years (Storer, 1864, First Outlines of a Dictionary of Chemical Solubilities, Sever and Francis, pp. 488–505). Such cations include cobalt, copper, nickel, and calcium (lime). Storer lists incorrect chemical formulas for these salts. This is a reflection of the poor state of technology in the year 1864. Correct formulas are provided in subsequent reference texts, such as the ubiquitous CRC Handbook of Chemistry and Physics (CRC Press).

It is known in the art of enzymology that numerous polyvalent elemental cations can substitute for magnesium (Mg$^{+2}$) in enzymatic reactions. In studying an enzyme, it is a common practice to determine which metal cofactors can substitute for Mg$^{+2}$. Metal cofactors which are commonly tested include manganese (Mn$^{+2}$), cobalt (Co$^{+2}$), zinc (Zn$^{+2}$), calcium (Ca$^{+2}$), and nickel (Ni$^{+2}$). Many enzymes are known which can substitute Mg$^{+2}$ with several other metal cofactors. For example, PDE-I can substitute Mg$^{+2}$ with Mn$^{+2}$, Zn$^{+2}$, and Ca$^{+2}$ (Razzel et al, 1959, Journal of Biological Chemistry, 234, 2109).

It is known in the art of enzymology that the presence of a metal cation in addition to Mg$^{+2}$ usually does not substantially inhibit the enzyme. For example, alkaline phosphatase is active in the presence of Mg$^{+2}$ plus any of the metal cations Co$^{+2}$, Mn$^{+2}$, Ca$^{+2}$, Ni$^{+2}$, Cd$^{+2}$ (Boyer, 1971, The Enzymes, third edition, Academic Press, v. 4, p. 441). PDE-I is active in the presence of Mg$^{+2}$ plus any of the metal cations Zn$^{+2}$, Pb$^{+2}$, Co$^{+2}$, Ni$^{+2}$, Fe$^{+3}$, Sn$^{+2}$, Ca$^{+2}$, Mn$^{+2}$, Ba$^{+2}$, and Cu$^{+2}$ (Razzel et al, 1959, Journal of Biological Chemistry, 234, 2109).

It is reasonable to infer from the known art of enzymology that the presence of such metal cations in an enzymatic reaction in addition to Mg$^{+2}$ is usually not deleterious.

For alkaline phosphatase, the metal cations which are known to be not deleterious are the same metal cations which are known to form highly insoluble salts with phosphate. These properties have never been synthesized with the known problem of phosphate inhibition of alkaline phosphatase. In addition to synthesizing these known elements, the inventor has made observations which have led to the present invention:

(a) Several polyvalent elemental cations were found which do not substantially inhibit any of the enzymatic reactions of the One Pot method, and (b) These polyvalent elemental cations can be used to precipitate phosphate selectively. That is, these cations do not significantly precipitate the enzyme substrates of the method.

Many polyvalent elemental cations form a poorly soluble salt with phosphate, and can be used in the present invention. Examples 1, 2, and 3 illustrate the use of several polyvalent elemental cations in the three modes of the One Pot method. Example 1 illustrates the Basic Mode. Example 2 illustrates the Reuse Mode. Example 3 illustrates the Preferred Mode. In each example in which the cation worked for a synthesis, a precipitate containing phosphate was formed with the cation. These cations and probably many others work for all three modes previously described by the inventor.

The only criteria for a useful precipitation cation is that the cation form a salt with phosphate which is poorly soluble in water. The inventor investigated which elemental cations had this property. Experiments were performed by the inventor to quantitate the solubility of phosphate salts in water of several elemental cations. The results are shown in the table below.

|  | $(PO_4)^{-3}$ | $(HPO_4)^{-2}$ | $(H_2PO_4)^{-1}$ |
| --- | --- | --- | --- |
| Li +1 | 100–120 mM | 20–40 mM | >500 mM |
| Na +1 | >250 mM | >330 mM | >500 mM |
| K +1 | >1000 mM | >1000 mM | >1000 mM |
| Rb +1 | >250 mM | >330 mM | >500 mM |
| Cs +1 | >250 mM | >330 mM | >500 mM |
| Mg +2 | 0.7 mM | 22 mM | >500 mM |
| Ca +2 | 0.2 mM | 1.1 mM | >500 mM |
| Zn +2 | 0.1 mM | 0.6 mM | >500 mM |
| Mn +2 | 0.2 mM | 0.7 mM | >500 mM |
| Co +2 | 0.1 mM | 0.9 mM | >330 mM |
| Ni +2 | 0.3 mM | 1.2 mM | >330 mM |
| Cu +2 | 0.1 mM | 0.4 mM | 5–10 mM |
| Sr +2 | 0.2 mM | 2.0 mM | >40 mM |
| Ba +2 | 0.3 mM | 1.7 mM | 20–40 mM |
| Fe +3 | 0.3 mM | <0.02 mM | 0.3 mM |
| Cr +3 | 1.0 mM | 0.4 mM | >250 mM |

The concentrations in the table refers to the concentration of $(cation^{+1})_3(PO_4)$, $(cation^{+2})_3(PO_4)_2$, $(cation^{+3})(PO_4)$, $(cation^{+1})_2(HPO_4)$, $(cation^{+2})(HPO_4)$, $(cation^{+3})_2(HPO_4)_3$ $(cation^{+1})(H_2PO_4)$, $(cation^{+2})(H_2PO_4)_2$, or $(cation^+3)(H_2PO_4)_3$. This data was obtained by diluting a concentrated solution of the $K^+$ salt of phosphate and a concentrated solution of the cation in water. Precipitation was established by the presence of a pellet after centrifugation. Many elements were not quantitated by the inventor and do not appear in table. Such elements may also be uselid in the invention. Three conclusions can be drawn from the data in the table, relevant to the present invention.

The first conclusion is that monovalent cations (i.e. having a charge of +1) alone cannot be used as a precipitation cation. Monovalent cations form salts with phosphate which are moderately or highly soluble in water. Polyvalent cations (i.e. having a charge greater than +1) can be used as precipitation cations. Polyvalent cations form salts with phosphate which are poorly soluble in water. The precipitates may also contain molecules of $H_2O$ and molecules of monovalent cations.

The second conclusion drawn from the table is that polyvalent elemental cations differ in their ability to precipitate phosphate. Cations which form extremely insoluble $HPO_4^{-2}$ salts, such as $Fe^{+3}$ are better at removing phosphate from solution than cations such as $Ca^{+2}$ which form poorly soluble salts with $HPO_4^{-2}$. For practical applications, this difference in solubility assumes a lesser importance. For example, if the cation is present at 10 mM excess over phosphate, the equilibrium solution phosphate concentration for either $Fe^{+3}$ or $Ca^{+2}$ will still be below 0.1 mM.

The third conclusion drawn from the table is that pH is a consideration for the proper use of some polyvalent elemental cations. For some polyvalent elemental cations, such as $Ca^{+2}$ and $Mn^{+2}$, the $HPO_4^{-2}$ salts are highly insoluble in water, but the $H_2PO_4^{-1}$ salts are highly soluble. The solution pH determines the equilibrium between $H_2PO_4^{-1}$ and $HPO_4^{-2}$. The pKa for $H_2PO_4^{-1}$ is about 6.8. Thus, obtaining a precipitate with such cations may require adjustment of the pH in order to form the $HPO_4^{-2}$ species in sufficient concentration. It is not necessary for the equilibrium to be greater than 99% $HPO_4^{-2}$ (e.g. pH 8.8) in order to obtain effective precipitation. For example, the inventor has determined that the solubility of the phosphate salts of $Mg^{+2}$, $Ca^{+2}$, $Mn^{+2}$, and $Zn^{+2}$ at pH 8.0 are approximately the same as the solubility of the pure $HPO_4^{-2}$ salt. Efficient $HPO_4^{-2}$ precipitation at near neutral pH occurs because the equilibrium concentration of $HPO_4^{-2}$ is sufficient to precipitate $CaHPO_4$. After $HPO_4^{-2}$ has precipitated, more $HPO_4^{-2}$ is formed, by deprotonation of $H_2PO_4^{-1}$, which then precipitates. The proton transfer allows most of the phosphate to precipitate. In addition, it is conceivable that the precipitated salt may be a mixture of $HPO_4^{-2}$ and $H_2PO_4^{-1}$. The researcher must determine if the precipitation is adequate for a given cation at a given pH. If it is not adequate, then either the pH can be increased or another cation may be used.

For other cations, such as $Fe^{+3}$, both $HPO_4^{-2}$ and $H_2PO_4^{-1}$ salts are poorly soluble in water. Solution pH is not a major consideration for phosphate precipitation in this case. However, since the $HPO_4^{-2}$ salt is usually less soluble, employing a pH which favors $HPO_4^{-2}$ is more effective at precipitating phosphate. It is also an empirical observation of the inventor that precipitation of $H_2PO_4^{-1}$ salts takes several minutes to occur; whereas, precipitation of $HPO_4^{-2}$ salts is usually instantaneous. This additional observation of precipitation rate is also a consideration in the invention. Rapid phosphate precipitation is preferred, since the precipitation process will not entail a longer cycle time in the synthesis method. In all cases tested by the inventor, precipitation of $HPO_4^{-2}$ occurs nearly instantly.

The pKa of $H_3PO_4$ is about 2. Therefore, at a pH below 2, none of the elemental cations will precipitate phosphate. However, since virtually all enzymatic reactions are conducted in a narrow pH range of about 5.0 to 11.0, there is no need to precipitate phosphate at such a low pH. The pKa for $HPO_4^{-2}$ is about 12. Increasing the pH above 12 deprotonates $HPO_4^{-2}$ to $PO_4^{-3}$. All polyvalent elemental cations precipitate $PO_4^{-3}$, as shown in the table. The need for precipitation of $PO_4^{-3}$ is probably rare, since most enzymatic reactions are rarely conducted above pH 11. An exception is the formation of minerals such as apetite, which contain $PO_4^{-3}$.

Magnesium as the Precipitation Cation

By previous practice of the One Pot method by the inventor, magnesium ($Mg^{+2}$) was used as the cofactor for the enzymes. As shown in the table, $MgHPO_4$ is moderately soluble in water at 22 mM. Surprisingly however, the inventor has discovered that $Mg^{+2}$ can be used to effectively precipitate phosphate. It is the observation of the inventor that the solubility of magnesium phosphate in water is highly dependent on pH. The solubility decreases as the pH increases. The solubility of magnesium phosphate at pH 8.0 is about 25 mM; however the solubility at pH 10.0 is about 3 mM. Thus, precipitating phosphate using magnesium is more effective at a high pH. The inventor hypothesizes that the phosphate in the magnesium phosphate precipitate is predominantly in the $PO_4^{-3}$ form, not the $HPO_4^{-2}$ form. The increase in pH perhaps increases the $PO_4^{-3}$ concentration sufficiently to form a $Mg^{+2}$ precipitate. Therefore, the One Pot method is preferably performed at a high pH, such as 10.0, in order to use magnesium as the precipitation cation. Using a high pH has the added advantage of increasing the activity of the enzymes AP and PDE-I.

Additional experiments by the inventor suggest that magnesium can be used at pH 8.0. Incubation of an aqueous solution of magnesium phosphate in 100 mM Tris-HCl, pH 8.0 at 60 degrees C. resulted in the precipitation of magnesium phosphate after one day of incubation. The calculated solubility of $MgHPO_4$ under these conditions was 3 mM. It is believed by the inventor that the precipitate was a magnesium phosphate crystalline mineral, such as newberyite. This suggests that by carefully selecting the conditions, or by seeding with the appropriate mineral crystals, magnesium can be used to effectively precipitate phosphate at near neutral pH.

Examples 4 and 5 illustrate the use of $Mg^{+2}$ as the precipitation cation in the Basic and Reuse modes respectively.

Spermine as the Precipitation Cation

Polyvalent elemental cations are not the only known substances which form poorly soluble salts in water with $HPO_4^{-2}$. Spermine also forms a poorly soluble salt with phosphate. Spermine has the chemical structure N,N'-bis[3-aminopropyl]-1,4-butanediamine and is commercially available from several vendors. Spermine is a member of the polyamine chemical family. The poor solubility of spermine phosphate in water was noted over 69 years ago by Dudley (Dudley et al, 1926, Biochemical Journal, 20, p. 1084 and p. 1093). The inventor's calculation of the solubility of spermine phosphate at room temperature is about 1 mM. This value is in agreement with the published solubility value (Merck Index).

The precipitation of phosphate by spermine behaves slightly differently from precipitation by polyvalent elemental cations. Spermine phosphate usually precipitates from aqueous solution in crystalline form; whereas polyvalent elemental cations usually precipitate in amorphous form. Spermine phosphate precipitation is greatly accelerated by seeding the solution with a tiny quantity of spermine phosphate crystals. Polyvalent elemental cations usually precipitate instantly. Thus, seeding is the preferred method for improving the rate of spermine phosphate precipitation. The inventor has determined that spermine phosphate precipitation does not co-precipitate oligonucleotides, in contrast to polyvalent elemental cations.

Spermine has several other advantages which make it especially useful for the invention. It is known in the literature that spermine by itself does not precipitate oligonucleotides, even at concentrations as high as 15 mM. Spermine is believed in the literature to protect nucleic acids from the free radical damage caused by oxygen radicals.

Interestingly, the literature teaches against the use of spermine in the presence of oligoribonucleotides (Kierzek, 1992, Nucleic Acids Research, 20, 5082-3). Kierzek reports that polyamines, such spermidine and polyvinylpyrrolydone, accelerates non-enzymatic oligoribonucleotide hydrolysis. Spermine is a polyamine. It is the observation of the inventor that this phenomenon either does not occur or that this phenomenon occurs at a trivial rate.

The structural aspects of spermine which allows the formation of a poorly soluble phosphate salt is not known in the art. Experiments performed by the inventor with other related polyamines=13 spermidine, putrescine, cadaverine, and ethylenediamine—demonstrate that they form highly soluble phosphate salts. Dudley was also surprised that a structure closely related to spermine did not form an insoluble phosphate salt:

"In connection with the extraordinary insolubility of spermine phosphate it is interesting to note that a base of similar structure, namely 'triethylenetetramine' $NH_2(CH_2)_2NH(CH_2)_2NH(CH_2)_2NH_2$ does not form an unusually insoluble phosphate" (Dudley et al, 1926, Biochemical Journal, 20, p. 1093).

Examples 6, 7, and 8 illustrate the use of spermine for the precipitation of phosphate in the present invention using the Basic mode, the Preferred Mode and the Reuse mode, respectively.

Other Cations as Precipitation Cations

It will be appreciated that other cations may be known in the literature or may be discovered in the future which can be useful as precipitation cations in the present invention. A useful precipitation cation should form a salt with phosphate which is poorly soluble in water. In addition, the cation preferably should not unduly inhibit the enzyme in the application. The acceptable level of enzyme inhibition is determined by the user.

Determining the solubility of a phosphate salt in water can be done in two ways. Both methods are well known techniques. In one method, the concentration of cation and phosphate in solution is increased slowly until a precipitate is observed. Precipitates are easiest to detect by centrifugation of the solution and determining the presence of an insoluble pellet. The solubility is calculated as the highest cation phosphate concentration which does not produce a pellet. In the other method, a saturated solution of the cation phosphate is prepared. The solubility of the cation phosphate is determined by measuring the concentration of cation phosphate in solution.

Accelerating Precipitation of Phosphate

Seeding is a well known technique for speeding the precipitation process from a supersaturated solution. Seeding may be usefully employed in the present invention for this purpose. For example, the inventor's experiments demonstrate that supersaturated solutions of spermine phosphate are slow to form initial crystals. After the first crystals are formed or are introduced externally by seeding, subsequent precipitation is rapid. Seeding may be useful in the invention for precipitating crystalline (mineral) forms of polyvalent elemental cation phosphate. Such minerals may include newberyite ($MgHPO_4$-$3H_2O$), monetite ($CaHPO_4$), brushite ($CaHPO_4$-$2H_2O$) and apetite form crystals.

Another useful technique for speeding precipitation is cooling the solution. This technique is especially useful for precipitating spermine phosphate, since the solubility of spermine phosphate is highly temperature dependent. For example, prior to phosphatase treatment the synthesis reaction could be incubated briefly at 4 degrees C. to accelerate spermine phosphate precipitation. Then the temperature can be increased to 25 degrees C. for the phosphatase incubation. Brief chilling followed by heating may form an undersaturated solution of the cation phosphate salt. This is expected if equilibration between solution and insoluble phases is slow. This may be useful in further lowering the solution phosphate concentration, below the thermodynamic equilibrium level.

Oligonucleotide Co-Precipitation

In using polyvalent elemental cations to precipitate phosphate, a small quantity of oligonucleotide may precipitate with the cation phosphate salt. This phenomenon is denoted as "co-precipitation" in the literature. Such co-precipitation is not desirable for the One Pot method, since it reduces the yield of final product. Oligonucleotide co-precipitation with $CaHPO_4$ is well established in the literature (Stenberg et al, 1982, Biochimica et Biophysica Acta, 697, 170-3). Co-precipitation of DNA with $CaHPO_4$ is an established method for introducing foreign DNA into mammalian cells. Although the literature describes co-precipitation, the literature does not teach or direct how to avoid co-precipitation.

One possible method is to precipitate the precipitation cation phosphate salt in the crystalline form, as opposed to the amorphous form. This may be accomplished by adjusting the buffer conditions, adjusting the temperature, adding additional ions, or seeding with crystals. Such crystalline forms are commonly called minerals. It is believed by the inventor that highly defined crystals of cation phosphate are far less able to co-precipitate oligonucleotides than the unstructured amorphous form. This theory is supported by the inventor's observation that no co-precipitation of oligonucleotide occurs with crystalline spermine phosphate precipitation. Some minerals may contain only polyvalent elemental cation and phosphate ions, such as monetite ($CaHPO_4$) and newberyite ($MgHPO_4$-$3H_2O$). Other minerals may contain other ions in addition to the polyvalent elemental cation and phosphate such as struvite ($MgNH_4PO_4$-$6H_2O$) and apetite. Other ions may include $OH^-$, $Cl^-$, $Br^-$, $F^-$, $K^+$, $Na^+$, and $NH_4^+$. Minerals are usually highly insoluble in water. Placing the appropriate ions in solution may allow the formation of a crystalline mineral.

Another method, devised by the inventor, to prevent oligonucleotide co-precipitation is the addition of a competitor substance. The competitor substance competes with the oligonucleotide for the binding sites on the cation phosphate precipitate. This competitor blocks these binding sites and prevents oligonucleotide co-precipitation. Two substances have been characterized as useful competitors by the inventor. Sulfate at a concentration of about 100 mM effectively eliminates oligonucleotide co-precipitation with $CaHPO_4$. A small phosphate concentration (5 to 10 mM) in excess of the cation concentration also effectively prevents oligonucleotide co-precipitation with $CaHPO_4$.

Other Oligonucleotide Synthesis Systems

The method of the invention may be applied to the synthesis of a portion of an oligonucleotide using a different chain extending enzyme, a different substrate, a different blocking group, and a different method for blocking group removal. This alternative system employs the chain extending enzyme Polynucleotide Phosphorylase (PNP) and the acetal blocking group, methoxyethanol (Mackey et al, 1971, Nature, 233, 551-3 ). The blocking group is removed chemically by mild acid treatment. In this synthetic method, phosphate by-product is generated by the PNP chain extension step in accordance with the reversible reaction: primer+ NDP-acetal< - - - >primer-pN-acetal+phosphate. This application of the invention is illustrated in example 9.

Sninsky recognized the reversible nature of the PNP coupling reaction and introduced a method for removing phosphate enzymatically (Sninsky et al, 1974, Nucleic Acids Research, 1, 1665–74). Phosphate was converted to ribose-1-phosphate in the presence of a nucleoside and the enzyme nucleoside phosphorylase. Sninsky's approach for "phosphate removal" was designed only in the context of improving the coupling efficiency of PNP. Sninsky's approach was not designed in the context of an enzymatic method in which cycles are performed without intermediate oligonucleotide purification. The Sninsky et al approach improved their previously described oligonucleotide synthesis method, a method which teaches intermediate oligonucleotide purification in each cycle (Mackey et al, 1971, Nature, 233, 551–553).

Sninsky's enzymatic phosphate removal method would not work for a One Pot method. Its main disadvantage is that the phosphate removal method is reversible. Phosphate is stored as ribose-1-phosphate. Phosphate would be released back into solution during the phosphatase step. The released phosphate would inhibit the phosphatase. Additional disadvantages of Sninky's approach are:

(a) inefficient phosphate removal. The equilibrium of the nucleoside phosphorylase reaction strongly favors the formation of free phosphate. Thus, Sninky's method could not keep the phosphate concentration at a low level.

(b) slow phosphate removal. By the nature of a kinetically slow enzymatic reaction, reaching equilibrium may take one hour.

(c) expensive. The enzyme nucleoside phosphorylase and the nucleoside are expensive.

In contrast to Sninsky's method, phosphate removal by precipitation in the present avoids these disadvantages. Most important is that phosphate removal by the present invention is not reversible. This makes the method suited for the One Pot method, in which no intermediate purifications are performed. In addition, the phosphate precipitation method is: (a) efficient at keeping phosphate concentration at micromolar levels, (b) instantaneous, and (c) inexpensive, since many of the cations are inexpensive.

Summary of the Invention for Oligonucleotide Synthesis

The present invention overcomes the disadvantage of previous methods for removing phosphate generated in an oligonucleotide synthesis. Previous methods entail oligonucleotide purification in each cycle to remove phosphate by-product. This method cannot be automated. The previous enzymatic removal method of Sninsky has poor operability. The present invention improves the operability of the One Pot method, previously described by the inventor. It overcomes the problem of phosphate by-product inhibition in a manner which allows unhindered performance of the One Pot method.

The benefit of the method of the invention increases with each successive cycle. For example, after 2 cycles, the soluble phosphate concentration may be 10 mM without using the invention and 0.1 mM using the invention. Thus, the benefit of the invention in this case is fair. However, after 10 cycles, the soluble phosphate concentration may be 50 mM without using the invention but still only 0.1 mM using the invention. Thus, the benefit of the invention in this case is large. The large benefit may be realized during a single cycle if a high phosphate concentration is generated during the cycle. This may occur if a high AppNp concentration is used in the One Pot method.

The preferred precipitation cation for the One Pot method depends on the type of oligonucleotide which is synthesized. For oligonucleotides which are stable at pH 10, the preferred precipitation cation is magnesium. For oligonucleotides which are not stable at pH 10, the preferred precipitation cation is spermine.

Scope of the Invention

The scope of the invention is not limited to the synthesis of oligonucleotides. The method of the invention may be employed to remove phosphate by-product generated in any enzymatic reaction by precipitating the phosphate. Numerous enzymes produce phosphate by-product, including phosphatases, nucleotidases, phosphorylases, and pyrophosphatases. For enzymes which are irreversible, such as phosphatases, the invention improves performance by removing phosphate inhibition on the enzymatic reaction. For enzymes which are reversible, such as polynucleotide phosphorylase, the invention improves the performance by removing phosphate by-product from solution, thus, driving the equilibrium towards product formation. The invention makes a reversible enzymatic reaction practically irreversible.

For example, the invention could be used to improve the manufacture of poly(A) from adenosine 5'-diphosphate using PNP, or to improve the manufacture of nucleosides from ribose-1-phosphate+purine base using nucleoside phosphorylase. The invention could improve alkaline phosphatase digestions, especially for high substrate concentrations. The invention is especially useful in multi-step enzymatic methods, whereby removal of the phosphate by precipitation avoids the need for an intermediate purification step to remove the phosphate.

The precipitation cation may be added to the solution before, during, or after the enzymatic reaction depending on the user's need. The cation may be added continuously or intermittently. It is preferred to add the cation at the start of the reaction. This allows phosphate removal as it is generated. Alternatively, the precipitation cation can be added at the end of the enzymatic reaction to precipitate out the phosphate. The reaction product may then be purified from the precipitate by filtration or centrifugation. In the event that the precipitation cation inhibits one or more enzymes in the solution, the cation should be added in a smaller quantity than the phosphate in solution. Cation may also be added in a manner which avoids a deleterious accumulation of the cation. The benefits of phosphate removal by precipitation should outweigh any negative effect of the cation.

For some applications, precipitation of the reaction product may be desirable in order to drive the enzymatic reaction forward. Precipitation of the product may occur with the precipitation cation alone or may occur by co-precipitation with the precipitation cation phosphate salt. For example, in the synthesis of poly(A) using ADP+PNP using $Ca^{+2}$ as the precipitation cation, the poly(A) product may co-precipitate with $CaHPO_4$. This contrasts with the One Pot method for synthesis of oligonucleotides, in which precipitation of the oligonucleotide product is usually not desirable.

The preferred precipitation cation depends highly on the specific application and the researcher's priorities. Characteristics of the cations should be weighed by the researcher. Such characteristics of the cation may include enzyme inhibition, cost, and human toxicity, environmental hazard, and disposal cost. In some circumstances, a mixture of more than one precipitation cation may be advantageous.

The present invention may also be used to remove pyrophosphate by-product, since salts of pyrophosphate are usually lower in solubility than phosphate. Numerous enzymes are known to generate pyrophosphate by-product, including polymerases and adenylylation enzymes. Applications may include dideoxy DNA sequencing, thermocycle dideoxy DNA sequencing, the polymerase chain reaction, and other DNA amplification methods which generate pyrophosphate by-product.

Conclusion of Phosphate Precipitation Method

In the context of any enzymatic reaction which generates phosphate by-product, the undesirable effect of the phosphate is well established in the literature. Previous approaches to the problem employ chromatographic purification or enzyme techniques to remove phosphate. The disadvantage of chromatographic purification is the inability to automate the method. The disadvantages of the enzymatic removal method are: (a) a slow rate of removal, (b) inefficient removal so that the phosphate concentration is not reduced to low levels, (c) reversibility of the removal, since the ribose-1-phosphate can re-release phosphate by the action of a phosphatase, and (d) need to chromatographically remove ribose-1-phosphate to prevent re-release. The disadvantage of the previous approach of the One Pot method is a loss of performance due to enzyme inhibition. The present invention overcomes these disadvantages by precipitating the phosphate. The precipitation method is by contrast (a) very fast, (b) highly efficient at lowering the solution phosphate concentration to micromolar levels, (c) not reversible, and (d) does not entail chromatographic or any physical separation from the reaction mixture.

In the history of the biochemical literature, it is possible that the conditions employed in an enzymatic reaction could have resulted in the formation of a precipitated phosphate salt. However, if such a precipitation did occur, it was never noted, explored, or exploited by the scientist. As a consequence, the advantageous nature of the phosphate precipitation is not known and has not been taught as a useful art.

NMP Inhibition of Phosphodiesterase I

In the One Pot method, the PDE-I incubation step generates nucleoside 5'-monophosphates (NMP's) by two previously described reactions. (PDE-I is also known by a different name, nucleotide pyrophosphatase).

(a) PDE-I generates adenosine 5'-monophosphate (AMP, which is an NMP) by the reaction: $AppNp+H_2O \rightarrow AMP+3',5'-NDP$, and (b) PDE-I generates NMP's by the reaction: $primer+xH_2O \rightarrow NMP's$.

It is known in the literature that NMP's inhibit PDE-I (Futai, 1967, Journal of Biological Chemistry, 242, p. 5306). However, the literature does not convey the severity of the NMP problem. The literature does not motivate the desirability for solving this problem. Experiments performed by the inventor demonstrate that the NMP inhibition problem is severe. The remaining PDE-I activity in the presence of 1 mM, 3 mM, and 10 mM AMP is 14%, 5%, and 2%, respectively.

The literature does not provide any direction to overcome the NMP inhibition problem. The inventor's previous solution was to use a sufficient PDE-I concentration for a sufficient incubation period to achieve complete substrate conversion. This previous approach had disadvantages. For example, if the AppNp concentration remaining after coupling was 10 mM, complete PDE-I hydrolysis would generate 10 mM AMP. By the previous approach to the problem, two solutions could be used. The first solution is to increase the PDE-I concentration; this would be expensive. The second solution is to prolong the PDE-I incubation period; this would increase the cycle time. Thus, neither solution is satisfactory.

It is the demonstration of the inventor that the inhibition of PDE-I by NMP's can be substantially eliminated by adding an additional enzyme during the PDE-I incubation. This additional enzyme is denoted an NMP degrading enzyme. The NMP degrading enzyme converts NMP's to a less inhibitory by-product. Three enzymes have been demonstrated as useful as NMP degrading enzymes: 5'-Nucleotidase, AMP Nucleosidase, and AMP Deaminase. The reactions catalyzed are:

5'-Nucleotidase: $NMP+H_2O \rightarrow nucleoside+HPO_4$

AMP Nucleosidase: $AMP+H_2O \rightarrow adenine+ribose-5'-phosphate$

AMP Deaminase: $AMP+H_2O \rightarrow inosine\ monophosphate+NH_3$

The products of these enzymes are less inhibitory to PDE-I than the substrate. For example, the remaining activity of PDE-I in the presence of 1 mM AMP is 14% activity; 1 mM adenosine is 89% activity; 1 mM ribose-5-phosphate+1 mM adenine is 86% activity; and 1 mM inosine monophosphate is 30% activity. From this data, 5'-Nucleotidase converts NMP's to the least inhibitory product, followed closely by AMP Nucleosidase. AMP Deaminase provides a small benefit. The preferred NMP degrading enzyme is 5'-Nucleotidase. 5'-Nucleotidase has the added benefit of hydrolyzing all NMP's. AMP Nucleosidase and Deaminase strongly favor AMP. The latter enzymes are still useful since most of the NMP will derive from reaction (a), which is AMP.

The use of an NMP degrading enzyme overcomes the severe NMP inhibition problem recognized by the inventor. Using either 5'-Nucleotidase or AMP Nucleosidase during PDE-I incubation in the One Pot method allows much more efficient PDE-I hydrolysis. AMP Deaminase provides a small improvement in PDE-I hydrolysis. The improved efficiency makes the PDE-I hydrolysis more reliable. It also allows the PDE-I incubation to be performed with less PDE-I enzyme, with a shorter incubation period, or both. Examples 3, 5, and 7 illustrates the use of 5'-Nucleotidase in the One Pot method. These enzymes were previously demonstrated as useful during the RNA Ligase incubation step. If the enzyme is not inactivated after RNA Ligase incubation, it can be used in the next step, the PDE-I incubation.

The NMP degrading enzyme may be used regardless of the use of the phosphate precipitation method. Phosphate is generated by using 5'-Nucleotidase as the NMP degrading enzyme. In this case, it is preferred to precipitate phosphate by a precipitation cation as it is generated. This substantially reduces phosphate inhibition of PDE-I and possible inhibition of 5'-Nucleotidase.

3',5'-NDP Inhibition of Phosphodiesterase I

The 3',5'-nucleoside diphosphate (3',5'-NDP) product of the PDE-I incubation, previously shown in reaction (a), also inhibits phosphodiesterase I (PDE-I). To the inventor's knowledge, there is no disclosure of 3',5'-NDP inhibition in the literature. This inhibition phenomenon is wholly the discovery of the inventor.

This inhibition may also reduce the performance of the PDE-I incubation. Experiments performed by the inventor demonstrate that the 3',5'-NDP inhibition problem is strong. The remaining PDE-I activity in the presence of 0.1 mM, 0.3 mM, and 1.0 mM 3',5'-ADP is 82%, 65%, and 34%, respectively. 3',5'-ADP is a weaker inhibitor than AMP. It is likely that all 3',5'-NDP's are weaker inhibitors than the corresponding NMP.

The 3',5'-NDP inhibition problem could be solved by using an enzyme combination to convert the 3',5'-NDP to a less inhibitory product. The enzyme combination should comprise 3',5'-bisphosphate nucleotidase+an NMP degrading enzyme. The enzyme 3',5'-bisphosphate nucleotidase (E.C. 3.1.3.7) catalyzes the reaction:

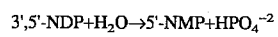

This enzyme was first characterized in 1958 by Brunngraber (Brunngraber, 1958, Journal of Biological Chemistry, 233, p. 475). It has also been characterized in liver, chlorella, and yeast. The gene coding for the yeast enzyme, called hal2, has been cloned and sequenced. Studies of the enzyme substrate specificity in liver indicate that it should work in the invention for the stated purpose. The enzymes is known to hydrolyze all four 3',5'-NDP's (A, G, C, and U). To work in the invention, the enzyme should not substantially dephosphorylate extended primer (primer-pNp). Ramaswamy's data demonstrates that the enzyme cannot hydrolyze phosphodiester bonds (ApA) or NADP (Ramaswamy, 1987, Journal of Biological Chemistry, 262, p. 10046). From this data, the inventor concludes that the enzyme is substantially inactive on extended primer.

The 5'-NMP product of the above reaction is converted to a less reactive product by using at least one NMP degrading enzyme in the enzyme combination. NMP degrading enzymes have been discussed previously. The preferred NMP degrading enzyme is 5'-Nucleotidase. 5'-Nucleotidase has the advantage of hydrolyzing all NMP's. In the presence of PDE-I+3',5'-bisphosphate nucleotidase+5'-Nucleotidase, AppNp substrate is converted to the least inihibitory products by the overall reaction:

The other NMP degrading enzymes, AMP Nucleosidase and AMP Deaminase, are less useful. NMP, derived from 3',5'-NDP, would be AMP only in a fraction of the cycles, i.e. only cycles using AppAp substrate. If the substrate is AppAp, using AMP Nucleosidase in the combination would convert 3',5'-ADP to less inhibitory products adenine+ribose-1-phosphate+$HPO_4^{-2}$. provides greater. Using AMP Deaminase in the combination would convert 3',5'-ADP to more inhibitory products inosine 5'-monophosphate+$HPO_4^-$ 2. Thus, AMP Nucleosidase is useful; whereas, AMP Deaminase is not a useful NMP degrading enzyme for 3',5'-ADP inhibition.

The enzyme combination may be used regardless of the use of the phosphate precipitation method. Phosphate is generated by 3',5'-bisphosphate nucleotidase using this method. It is preferred to precipitate phosphate by a precipitation cation as it is generated. This substantially reduces phosphate inhibition of PDE-I and possible inhibition of 3',5'-bisphosphate nucleotidase.

Example 10 illustrates a hypothetical use of the method for reducing the inhibition of 3',5-NDP by using an enzyme combination.

The method of the invention will now be further described by way of the following, non-limiting examples.

EXAMPLE 1

Basic Mode of One Pot Method using Polyvalent Elemental Cations

The oligonucleotide ApApCpApA was synthesized using the primer ApApC and two cycles of the Basic Mode of the One Pot method using the substrate AppAp. In this example and in subsequent examples, AppAp was formed in the reaction mixture by RNA Ligase from precursors ATP and 3',5'-ADP. In this example and in subsequent examples, dithiothreitol was not added to the synthesis buffer, since dithiothreitol is known to strongly inhibit alkaline phosphatase and phosphodiesterase I. In the Basic Mode, alkaline phosphatase both inactivates nucleotide substrate and removes the blocking group from the blocked primer product. The reaction was performed in a 20 ul volume containing 100 mM Tris-HCl, pH 8.0, 10 mM $MgCl_2$, 0.01% TRITON X-100™ (Union Carbide, Inc.), 0.5 mM ApApC primer, and 10 mM elemental salt. The cation of the elemental salt was used to precipitate phosphate generated by the synthesis method. The synthesis procedure below was performed for each of the following elemental salts: $CaCl_2$, $MnCl_2$, $ZnCl_2$, $SrCl_2$, $BaCl_2$, $COCl_2$, $CuCl_2$, $NiCl_2$, $FeCl_3$, and $CrCl_3$.

cycle 1
  (1) Add 0.4 ul 100 mM ATP+0.55 ul 90 mM 3',5'-ADP+1 ul (20 units) T4 RNA Ligase (New England Biolabs), incubate at 37 degrees C. for 2 hours, heat inactivate at 65 degrees C. for 5 minutes, cool to room temperature.
  (2) Add 1 ul (1 unit) Alkaline Phosphatase (calf intestine, U.S. Biochemical Corp.), incubate at 37 degrees C. for 1 hour.

Precipitates with phosphate were formed in all the syntheses. A 2 ul aliquot of the reaction mixture was analyzed by high pressure liquid chromatography (HPLC) on an HQ/M anion exchange column (Perseptive Biosystems) using a 0M to 1.0M NaCl linear gradient to quantitate the yield of ApApCpA product. A good yield was obtained for syntheses employing $Ca^{+2}$, $Mn^{+2}$, $Sr^{+2}$, $Ba^{+2}$, $Co^{+2}$, $Ni^{+2}$, $Fe^{+3}$, and $Cr^{+3}$. The cations $Zn^{+2}$ and $Cu^{+2}$ gave virtually no yield. Precipitation was even observed for some of the syntheses during the first step of the cycle, presumably due to precipitation of pyrophosphate formed as a by-product of the RNA Ligase reaction.

The product of the first cycle, ApApCpA, served as the primer for a second cycle of AppAp coupling. The reaction mixture was first heated at 95 degrees C. for 5 minutes to inactivate alkaline phosphatase. The second cycle procedure was the same as the first cycle. In addition, 1 ul 200 mM cation salt was added, and the alkaline phosphatase incubation was continued for 90 minutes. This added measure ensured that all the phosphate was precipitated and that the dephosphorylation reaction was 100% complete. These two cycles were performed without any intermediate purification of oligonucleotide product. A 5 ul aliquot of the reaction mixture was analyzed by HPLC as described to quantitate ApApCpApA yield. Syntheses which employed the cations $Ca^{+2}$, $Mn^{+2}$, $Sr^{+2}$, and $Ba^{+2}$ gave good product yields. The synthesis with $Co^{+2}$ gave a poor product yield. The syntheses employing $Ni^{+2}$, $Fe^{+3}$, and $Cr^{+3}$ resulted in virtually no product.

For syntheses in which the product yield was either poor or non-existent, it is the belief of the inventor that there are three possible causes: (1) The cation caused a strong inhibition of RNA Ligase, resulting in poor coupling efficiency, and a poor product yield, (2) The cation precipitated the substrates of a reaction ATP/3',5'-ADP/primer/primer-pNp, preventing the enzyme from catalyzing the conversion to product, (3) the cation precipitated the product, or (4) the cation co-precipitated the product. If the product was precipitated, then the synthesis was successful but the HPLC would not record it as successful. The HPLC analysis was performed on an aliquot by first removing the precipitate from the aliquot prior to injection into the chromatographic column, to avoid column clogging.

EXAMPLE 2

Reuse Mode of One Pot Method using Polyvalent Elemental Cations

The oligonucleotide ApApCpApA was synthesized using the primer ApApC and two cycles of the One Pot method. The first cycle couples AppAp to primer using the Reuse Mode of the One Pot method. In this cycle, uncoupled AppAp substrate is not inactivated so that it can be reused for the second cycle. The second cycle couples AppAp, derived from the first cycle, to primer using the Basic Mode. No AppAp was added for the second cycle. The reaction was performed in a 20 ul volume containing 100 mM Tris-HCl, pH 8.0, 10 mM $MgCl_2$, 0.01% TRITON X-100™, 0.5 mM ApApC primer, and 10 mM elemental salt. The cation of the elemental salt was used to precipitate phosphate generated by the synthesis method. The synthesis procedure below was performed for each of the following elemental salts to demonstrate their utility: $CaCl_2$, $MnCl_2$, $SrCl_2$, $BaCl_2$, $COCl_2$, $NiCl_2$, $FeCl_3$, and $CrCl_3$.

cycle 1
  (1) Add 0.4 ul 100 mM ATP+0.55 ul 90 mM 3',5'-ADP+1 ul (20 units) T4 RNA Ligase (New England Biolabs), incubate at 37 degrees C. for 5 hours, heat inactivate at 65 degrees C. for 5 minutes, cool to room temperature.
  (2) Add 1 ul (0.8 units) Polynucleotide Kinase-3'-Phosphatase (New England Biolabs), incubate at 37 degrees C. for 2 hours. To ensure complete primer deblocking and 5' phosphorylation, 1 ul (10 units) Polynucleotide Kinase-3'-Phosphatase+1 ul 40 mM ATP was subsequently added and incubated at 37 degrees C. for 8 hours to form pApApCpA product.

Precipitates with phosphate were formed in all these syntheses. A 2 ul aliquot of the reaction mixture was analyzed by HPLC as in example 1. The product pApApCpA was obtained in good yield for syntheses employing the polyvalent elemental cations: $Ca^{+2}$, $Mn^{+2}$, $Sr^{+2}$, $Ba^{+2}$, $Fe^{+3}$, and $Cr^{+3}$. Poor product yields were and $Ni^{+2}$.

The product of the first cycle, pApApCpA, served as the primer for a second cycle of AppAp coupling, without adding AppAp substrate. The reaction mixture was first heated at 75 degrees C. for 5 minutes to inactivate Polynucleotide Kinase-3'-Phosphatase. The Basic Mode procedure was used for the second cycle as follows:

cycle 2
  (1) Add 1 ul (20 units) T4 RNA Ligase, incubate at 37 degrees C. for 5 hours, heat inactivate at 65 degrees C. for 5 minutes, cool to room temperature.
  (2) Add 1 ul (1 unit) Alkaline Phosphatase (calf intestine, U.S. Biochemical Corp), incubate at 37 degrees for 1 hour.

A 5 ul aliquot of the reaction mixture was analyzed by HPLC as described to determine the yield of ApApCpApA product. Syntheses using $Ca^{+2}$, $Mn^{+2}$, $Sr^{+2}$, and $Ba^{+2}$ each resulted in a good product yield. Syntheses using $Co^{+2}$, $Fe^{+3}$, and $Cr^{+3}$ each resulted in a poor product yield. The synthesis using $Ni^{+2}$ resulted in virtually no product.

EXAMPLE 3

Preferred Mode of One Pot Method using Polyvalent Elemental Cations

The oligonucleotide ApApCpApA was synthesized using the primer ApApC and two cycles of the Preferred Mode of the One Pot method using the substrate AppAp. The reaction was performed in a 20 ul volume containing 100 mM Tris-HCl, pH 8.0, 10 mM $MgCl_2$, 0.01% TRITON X-100™, and 0.5 mM ApApC primer. The cation of the elemental salt was used to precipitate phosphate generated by the synthesis method. The synthesis procedure below was performed for each of the following elemental salts: $CaCl_2$, $MnCl_2$, $SrCl_2$, $BaCl_2$, $COCl_2$, $NiCl_2$, $FeCl_3$, and $CrCl_3$.

cycle 1
  (1) Add 1 ul 200 mM elemental salt+0.4 ul 100 mM ATP+0.5 ul 100 mM 3',5' -ADP+1 ul (20 units) T4 RNA Ligase (New England Biolabs), incubate at 37 degrees C. for 6 hours, heat inactivate at 65 degrees C. for 5 minutes, cool to room temperature.

(2) Add 1 ul (0.001 units) Phosphodiesterase I (snake venom, also known as Nucleotide Pyrophosphatase, U.S. Biochemical Corp)+1 ul (0.05 units) 5'-Nucleotidase (snake venom, Sigma Chemical), incubate at 37 degrees C. for 1 hour, heat inactivate at 85 degrees for 5 minutes, cool to room temperature.

(3) Add 1 ul (1 unit) Alkaline Phosphatase (calf intestine, U.S. Biochemical Corp.), incubate at 55 degrees C. for 1 hour, heat inactivate at 95 degrees for 5 minutes, cool to room temperature.

Precipitates with phosphate were formed in all these syntheses. A 2 ul aliquot of the reaction mixture was analyzed by HPLC to quantitate the yield of ApApCpA product. A good yield was obtained for syntheses employing $Ca^{+2}$, $Mn^{+2}$, $Sr^{+2}$, $Ba^{+2}$, $Co^{+2}$, and $Fe^{+3}$. The cations $Ni^{+2}$ and $Cr^{+3}$ gave virtually no yield. Precipitation was even observed for some of the syntheses during the first step of the cycle, presumably due to precipitation of pyrophosphate formed as a by-product of the RNA Ligase reaction.

The product of the first cycle, ApApCpA, served as the primer for a second cycle of AppAp coupling. The second cycle procedure was the same as the first cycle. These two cycles were performed without any intermediate purification of oligonucleotide product. A 10 ul aliquot of the reaction mixture was analyzed by HPLC as described to quantitate ApApCpApA product yield. Syntheses which employed the cations $Ca^{+2}$, $Mn^{+2}$, $Sr^{+2}$, and $Ba^{+2}$ gave good a product yield. The observed yield from highest to lowest was $Sr^{+2}>Ba^{+2}>Ca^{+2}>Mn^{+2}$. The syntheses employing $Co^{+2}$, $Ni^{+2}$, $Fe^{+3}$, and $Cr^{+3}$ resulted in no product.

EXAMPLE 4

Basic Mode of the One Pot Method using Magnesium

The oligonucleotide ApApCpApA was synthesized using the primer ApApC and two cycles of the Basic Mode using the substrate AppAp. The reaction was performed in a 20 ul volume containing 100 mM 3-cyclohexylamino-2-hydroxy-1-propanesulfonic acid, pH 10.0, 10 mM $MgCl_2$, 0.01% TRITON X-100™, and 0.5 mM ApApC primer. Magnesium was used to precipitate phosphate generated by the synthesis method. The synthesis procedure below was performed. The buffer salt in this example has the additional advantage that the pH decreases rapidly to a more neutral pH upon heating the solution. This reduces the probability of alkaline hydrolysis of the oligonucleotide during heating.

cycle 1

(1) Add 0.4 ul 100 mM ATP+0.5 ul 100 mM 3',5'-ADP+1 ul (20 units) T4 RNA Ligase (New England Biolabs), incubate at 37 degrees C. for 2 hours, heat inactivate at 65 degrees C. for 5 minutes, cool to room temperature.

(2) Add 0.5 ul (0.5 unit) Alkaline Phosphatase (calf intestine, U.S. Biochemical Corp.), incubate at room temperature for 1 hour, heat inactivate at 95 degrees for 5 minutes, cool to room temperature.

A precipitate was present in the reaction mixture, believed to be magnesium phosphate. A 2 ul aliquot of the reaction mixture was analyzed by HPLC and confirmed the synthesis of the desired product, ApApCpA. This product served as the primer for a second cycle of AppAp coupling. The second cycle procedure was performed as follows.

cycle 2

(1) Add 0.4 ul 100 mM ATP+0.5 ul 100 mM 3',5'-ADP+1 ul 200 mM $MgCl_2$2 ul (40 units) T4 RNA Ligase, incubate at 37 degrees for 5.5 hours, heat inactivate at 65 degrees C. for 5 minutes, cool to room temperature.

(2) Add 1 ul (1 unit) Alkaline Phosphatase, incubate at room temperature for 2.5 hours.

These two cycles were performed without any intermediate purification of oligonucleotide product. A precipitate was present in the reaction mixture, believed to be magnesium phosphate. A 10 ul aliquot of the reaction mixture was analyzed by HPLC and confirmed the synthesis of the desired product, ApApCpApA

EXAMPLE 5

Preferred Mode of the One Pot Method using Magnesium

The oligonucleotide ApApCpApA was synthesized using the primer ApApC and two cycles of the Preferred Mode using the substrate AppAp. The reaction was performed in a 20 ul volume containing 100 mM 3-cyclohexylamino-2-hydroxy-1-propanesulfonic acid, pH 10.0, 10 mM $MgCl_2$, 0.01% TRITON X-100™, and 0.5 mM ApApC primer. Magnesium was used to precipitate phosphate generated by the synthesis method. The synthesis procedure below was performed.

cycle 1

(1) Add 0.4 ul 100 mM ATP+0.5 ul 100 mM 3',5'-ADP+1 ul (20 units) T4 RNA Ligase (New England Biolabs), incubate at 37 degrees C. for 2 hours, heat inactivate at 65 degrees C. for 5 minutes, cool to room temperature.

(2) Add 0.5 ul (0.0005 units) Phosphodiesterase I (snake venom, U.S. Biochemical Corp)+1 ul (0.05 units) 5'-Nucleotidase (snake venom, Sigma Chemical), incubate at 37 degrees C. for 1 hour, heat inactivate at 85 degrees for 5 minutes, cool to room temperature.

(3) Add 0.5 ul (0.5 unit) Alkaline Phosphatase (calf intestine, U.S. Biochemical Corp.), incubate at room temperature for 1 hour, heat inactivate at 95 degrees for 5 minutes, cool to room temperature.

A precipitate was present in the reaction mixture, believed to be magnesium phosphate. A 2 ul aliquot of the reaction mixture was analyzed by HPLC and confirmed the synthesis of the desired product, ApApCpA. This product served as the primer for a second cycle of AppAp coupling. The second cycle procedure was performed as follows.

cycle 2

(1) Add 0.4 ul 100 mM ATP+0.5 ul 100 mM 3',5'-ADP+1 ul 200 mM $MgCl_2$+2 ul (40 units) T4 RNA Ligase, incubate at 37 degrees C. for 4 hours, heat inactivate at 65 degrees C. for 5 minutes, cool to room temperature.

(2) Add 0.5 ul (0.0005 units) Phosphodiesterase I+1 ul (0.05 units) 5'-Nucleotidase, incubate at 37 degrees C. for 1 hour, heat inactivate at 85 degrees for 5 minutes, cool to room temperature.

(3) Add 1 ul (1 unit) Alkaline Phosphatase, incubate at room temperature for 2.5 hours.

These two cycles were performed without any intermediate purification of oligonucleotide product. A precipitate was present in the reaction mixture, believed to be magnesium phosphate. A 10 ul aliquot of the reaction mixture was analyzed by HPLC and confirmed the synthesis of the desired product, ApApCpApA.

EXAMPLE 6

Basic Mode of the One Pot Method using Spermine

The oligonucleotide ApApCpApA was synthesized using the primer ApApC and two cycles of the Basic Mode using the substrate AppAp. The reaction was performed in a 20 ul volume containing 100 mM Tris-HCl, pH 8.0, 10 mM MgCl$_2$, 0.01% TRITON X-100™, 20 mM spermine-4HCl, and 0.5 mM ApApC primer. Spermine was used to precipitate phosphate generated by the synthesis method. The seeding technique was used to speed precipitation. The synthesis procedure below was performed.

cycle 1
(1) Add 0.4 ul 100 mM ATP+0.5 ul 100 mM 3',5'-ADP+2 ul (40 units) T4 RNA Ligase (New England Biolabs), incubate at 37 degrees C. for 4.5 hours, heat inactivate at 65 degrees C. for 5 minutes, cool to room temperature.
(2) Add 1 ul 10 mM spermine phosphate suspension+1 ul (1 unit) Alkaline Phosphatase (calf intestine, U.S. Biochemical Corp.), incubate at 55 degrees for 1 hour, add an additional 1 ul 10 mM spermine phosphate suspension, continue incubation at room temperature for 1 hour, heat inactivate at 95 degrees for 5 minutes, cool to room temperature.

A 2 ul aliquot of the reaction mixture was analyzed by HPLC and confirmed the synthesis of the desired product, ApApCpA. This product served as the primer for a second cycle of AppAp coupling. The second cycle procedure was performed as follows.

cycle 2
(1) Add 0.4 ul 100 mM ATP+0.5 ul 100 mM 3',5'-ADP+2 ul (40 units) T4 RNA Ligase incubate at 37 degrees for 4.5 hours, heat inactivate at 65 degrees C. for 5 minutes, cool to room temperature.
(2) Add 1 ul 10 mM spermine phosphate suspension+1 ul (1 unit) Alkaline Phosphatase, incubate at room temperature for 2.5 hours.

These two cycles were performed without any intermediate purification of oligonucleotide product. A 10 ul aliquot of the reaction mixture was analyzed by HPLC and confirmed the synthesis of the desired product, ApApCpApA

EXAMPLE 7

Preferred Mode of the One Pot Method using Spermine

The oligonucleotide ApApCpApA was synthesized using the primer ApApC and two cycles of the Preferred Mode using the substrate AppAp. The reaction was performed in a 20 ul volume containing 100 mM Tris-HCl, pH 8.0, 10 mM MgCl$_2$, 0.01% TRITON X-100™, 20 mM spermine-4HCl, and 0.5 mM ApApC primer. Spermine was used to precipitate phosphate generated by the synthesis method. The seeding technique was used to speed precipitation. The synthesis procedure below was performed.

cycle 1
(1) Add 0.4 ul 100 mM ATP+0.5 ul 100 mM 3',5'-ADP+2 ul (40 units) T4 RNA Ligase (New England Biolabs), incubate at 37 degrees C. for 3.5 hours, heat inactivate at 65 degrees C. for 5 minutes, cool to room temperature.
(2) Add 1 ul (0.001 units) Phosphodiesterase I (snake venom, US Biochemical Corp)+1 ul (0.05 units) 5'-Nucleotidase (snake venom, Sigma Chemical), incubate at 37 degrees C. for 1 hour, heat inactivate at 85 degrees C. for 5 minutes, cool to room temperature.
(3) Add 1 ul 10 mM spermine phosphate suspension+1 ul (1 unit) Alkaline Phosphatase (calf intestine, U.S. Biochemical Corp.), incubate at 55 degrees C. for 1 hour, add an additional 1 ul 10 mM spermine phosphate suspension, continue incubation at room temperature for 1 hour, heat inactivate at 95 degrees for 5 minutes, cool to room temperature.

A 2 ul aliquot of the reaction mixture was analyzed by HPLC and confirmed the synthesis of the desired product, ApApCpA. This product served as the primer for a second cycle of AppAp coupling. The second cycle procedure was performed as follows.

cycle 2
(1) Add 0.4 ul 100 mM ATP+0.5 ul 100 mM 3',5'-ADP+2 ul (40 units) T4 RNA Ligase incubate at 37 degrees C. for 3.5 hours, heat inactivate at 65 degrees C. for 5 minutes, cool to room temperature.
(2) Add 1 ul (0.001 units) Phosphodiesterase I+1 ul (0.05 units) 5'-Nucleotidase, incubate at 37 degrees C. for 1 hour, heat inactivate at 85 degrees for 5 minutes, cool to room temperature.
(3) Add 1 ul 10 mM spermine phosphate suspension+1 ul (1 unit) Alkaline Phosphatase, incubate at room temperature for 2.5 hours.

These two cycles were performed without any intermediate purification of oligonucleotide product. A 10 ul aliquot of the reaction mixture was analyzed by HPLC and confirmed the synthesis of the desired product, ApApCpApA.

EXAMPLE 8

Reuse Mode of One Pot Method using Spermine

The oligonucleotide ApApCpApA was synthesized using the primer ApApC and two cycles of the One Pot method. The first cycle couples AppAp to primer using the Reuse Mode. In this cycle, uncoupled. AppAp substrate is not inactivated so that it can be reused for the second cycle. The second cycle couples AppAp, derived from the first cycle, to primer using the Basic Mode. No AppAp was added for the second cycle. The reaction was performed in a 20 ul volume containing 100 mM Tris-HCl, pH 8.0, 10 mM MgCl$_2$, 0.01% TRITON X-100™, 20 mM spermine-4HCl, and 0.5 mM ApApC primer. Spermine was used to precipitate phosphate generated by the synthesis method. The seeding technique was used to speed precipitation. The synthesis procedure below was performed.

cycle 1
(1) Add 0.4 ul 100 mM ATP+0.5 ul 100 mM 3',5'-ADP+2 ul (40 units) T4 RNA Ligase (New England Biolabs), incubate at 37 degrees C. for 4.5 hours, heat inactivate at 65 degrees C. for 5 minutes, cool to room temperature.
(2) Add 1 ul 10 mM spermine phosphate suspension+1 ul (10 units) Polynucleotide Kinase-3'-Phosphatase (New England Biolabs), incubate at 37 degrees C. for 1 hour, add an additional 1 ul 10 mM spermine phosphate suspension, continue incubation at room temperature for 1 hour, heat inactivate at 75 degrees for 5 minutes, cool to room temperature.

The product of the first cycle, pApApCpA, served as the primer for a second cycle of AppAp coupling, without adding AppAp substrate in cycle 2. The Basic Mode procedure was used for the second cycle as follows:

cycle 2
(1) Add 2 ul (40 units) T4 RNA Ligase, incubate at 37 degrees C. for 4.5 hours, heat inactivate at 65 degrees C. for 5 minutes, cool to room temperature.
(2) Add 1 ul 10 mM spermine phosphate suspension+1 ul (1 unit) Alkaline Phosphatase (calf intestine, U.S. Biochemical Corp), incubate at room temperature for 2.5 hours.

These two cycles were performed without any intermediate purification of oligonucleotide product. A 10 ul aliquot of the reaction mixture was analyzed by HPLC and confirmed the synthesis of the desired product, ApApCpApA.

EXAMPLE 9

One Cycle of Basic Mode using a different Chain Extending Enzyme

The oligonucleotide ApApCpC was synthesized using the primer ApApC and one cycle of the Basic Mode of the One Pot method using polynucleotide phosphorylase as the chain extending enzyme and using CDP-2'-acetal methoxyethanol as the nucleotide substrate (obtained from Dr. P. Gilham, Purdue University, U.S.A.). Alkaline phosphatase inactivated nucleotide substrate, and acid treatment removed the blocking group from the primer-blocked nucleotide product. The reaction was performed in a 20 ul volume containing 25 mM Tris-HCl, pH 8.0, 10 mM $MgCl_2$, 0.01% TRITON X-100™, 10 mM elemental salt, and 0.5 mM ApApC primer. The cation of the elemental salt was used to precipitate phosphate generated by the synthesis method. The synthesis procedure below was performed for each of the following elemental salts: $CaCl_2$, $MnCl_2$, $ZnCl_2$, $SrCl_2$, $BaCl_2$, $CoCl_2$, $NiCl_2$, $CuCl_2$, $FeCl_3$, and $CrCl_3$.

cycle 1
(1) Add 1.1 ul 46 mM CDP-2'-acetal+1 ul (0.44 units) polynucleotide phosphorylase (M. luteus, Sigma Chemical), incubate at 37 degrees C. for 2.5 hours, heat inactivate at 85 degrees C. for 5 minutes, cool to room temperature.
(2) Add 1 ul (1 unit) alkaline phosphatase (calf intestine, U.S. Biochemical Corp.), incubate at 55 degrees C. for 1 hour. This step inactivates CDP-acetal.
(3) Add 1 ul 0.25M HCl, incubate at 95 degrees C. for 5 minutes, cool to room temperature. Add 1 ul 0.25M NaOH to neutralize the acid. This step removes the acetal blocking group from extended primer and inactivates alkaline phosphatase.

A 2 ul aliquot of the reaction mixture was analyzed by HPLC to quantitate the yield of ApApCpC product. A good yield was obtained for syntheses employing $Ca^{+2}$, $Mn^{+2}$, $Sr^{+2}$, $Ba^{+2}$, and $Co^{+2}$. A poor yield was obtained for the synthesis employing $Ni^{+2}$. These syntheses formed a precipitate with phosphate. The cations $Zn^{+2}$, $Cu^{+2}$, $Fe^{+3}$ and $Cr^{+3}$ gave no detectable yield.

EXAMPLE 10

Hypothetical Illustration of method for reduction of 3',5'-NDP inhibition

The same method could be performed as in examples 3, 5, and 7, except that the enzyme 3',5'-bisphosphate nucleotidase would be used during the PDE-I incubation of step 2. This method could also be used in the absence of the phosphate precipitation method. This would be done using the same procedure as example 7, except that spermine would not be added.

I claim:

1. A method for synthesizing a portion of an oligonucleotide of defined sequence comprising a cycle of synthetic steps:

(a) combining an oligonucleotide primer and a blocked nucleotide in a reaction mixture in the presence of a chain extending enzyme, such that a primer-blocked nucleotide product is formed, wherein the blocked nucleotide comprises (i) a nucleotide to be added to form part of the defined sequence and (ii) a blocking group attached to the nucleotide effective to prevent the addition of more than one blocked nucleotide to the primer; and (b) removing the blocking group from the 3' end of the primer-blocked nucleotide product to form a primer-nucleotide product;

whereby phosphate is generated in at least one synthetic step;

whereby a precipitate is formed; and whereby said precipitate comprises phosphate and at least one precipitation cation.

2. A method according to claim 1, further comprising the synthetic step (c) of inactivating unreacted blocked nucleotide by converting the unreacted blocked nucleotide to form which is less active as a substrate for the chain extending enzyme, wherein the unreacted blocked nucleotide is blocked nucleotide by converting the unreacted blocked nucleotide to a form which is less active as a substrate for the chain extending enzyme, wherein the unreacted blocked nucleotide is blocked nucleotide, which did not couple to the primer in step (a).

3. A method according to claim 2, wherein a second cycle of synthetic steps (a), (b), and (c) is performed using the primer-nucleotide product of step (b) in the first cycle as the primer of step (a) in the second cycle, and wherein blocked nucleotide is added for coupling in the second cycle, and wherein both cycles are performed without an additional intermediate step of purifying primer-blocked nucleotide or primer-nucleotide.

4. A method according to claim 3, wherein the chain extending enzyme is RNA Ligase.

5. A method according to claim 4, wherein the blocking group is a 3'-phosphate monoester, and the blocking group is removed using phosphatase.

6. A method according to claim 5, wherein the blocked nucleotide has the formula AppNp, wherein N represents a nucleoside or nucleoside analog, wherein RNA Ligase can couple the AppNp to the oligonucleotide primer, and wherein the primer-pN product is able to serve as a primer for RNA Ligase.

7. A method according to claim 6, wherein the unreacted blocked nucleotide is inactivated using nucleotide pyrophosphatase.

8. A method according to claim 7, wherein the nucleotide pyrophosphatase incubation is performed in the presence of a nucleoside 5'-monophosphate degrading enzyme, whereby nucleoside 5'-monophosphate is converted to a form which is less inhibitory to nucleotide pyrophosphatase.

9. A method according to claim 8, wherein the nucleoside 5'-monophosphate degrading enzyme is 5'-Nucleotidase.

10. A method according to claim 8, wherein the nucleoside 5'-monophosphate degrading enzyme is AMP Nucleosidase and the nucleoside 5'-monophosphate is adenosine 5'-monophosphate.

11. A method according to claim 9, wherein the incubation is performed in the presence of 3',5'-bisphosphate nucleotidase, whereby 3',5'-nucleoside diphosphate is converted to a form, nucleoside+two phosphates, which is less inhibitory to nucleotide pyrophosphatase.

12. A method according to claim 2, wherein the precipitation cation is a polyvalent elemental cation.

13. A method according to claim 3, wherein the precipitation cation is a polyvalent elemental cation.

14. A method according to claim 4, wherein the precipitation cation is a polyvalent elemental cation.

15. A method according to claim 5, wherein the precipitation cation is a polyvalent elemental cation.

16. A method according to claim 6, wherein the precipitation cation is a polyvalent elemental cation.

17. A method according to claim 7, wherein the precipitation cation is a polyvalent elemental cation.

18. A method according to claim 2, wherein the precipitation cation is spermine.

19. A method according to claim 3, wherein the precipitation cation is spermine.

20. A method according to claim 4, wherein the precipitation cation is spermine.

21. A method according to claim 5, wherein the precipitation cation is spermine.

22. A method according to claim 6, wherein the precipitation cation is spermine.

23. A method according to claim 7, wherein the precipitation cation is spermine.

24. A method for improving the performance of an enzymatic reaction in a reaction mixture, whereby the reaction mixture comprises:

(a) at least one enzyme, (b) at least one precipitation cation, and (c) at least one substrate for said enzyme, whereby phosphate is generated by the action of the enzyme on the substrate;

whereby a precipitate is formed, said precipitate comprising the precipitation cation and phosphate.

25. A method according to claim 24, wherein the precipitation cation is a polyvalent elemental cation.

26. A method according to claim 24, wherein the precipitation cation is spermine.

27. A method for reducing the inhibition of at least one nucleoside 5'-monophosphate on phosphodiesterase I, comprising incubating phosphodiesterase I in the presence of at least one nucleoside 5'-monophosphate degrading enzyme, whereby the nucleoside 5'-monophosphate is converted to a form which is less inhibitory to phosphodiesterase I.

28. A method according to claim 27, wherein the nucleoside 5'-monophosphate degrading enzyme is 5'-Nucleotidase.

29. A method according to claim 27, wherein the nucleoside 5'-monophosphate degrading enzyme is AMP Nucleosidase and the nucleoside 5'-monophosphate is adenosine 5'-monophosphate.

30. A method according to claim 27, further comprising the presence of 3',5'-bisphosphate nucleotidase, whereby 3',5'-nucleoside diphosphate is converted to a form which is less inhibitory to phosphodiesterase I.

31. A method according to claim 30, wherein the nucleoside 5'-monophosphate degrading enzyme is 5'-Nucleotidase.

32. A method according to claim 30, wherein the 3',5'-nucleoside diphosphate is 3',5'adenosine diphosphate and the nucleoside 5'-monophosphate degrading enzyme is AMP Nucleosidase.

* * * * *